United States Patent [19]
Ence

[11] Patent Number: 6,005,662
[45] Date of Patent: *Dec. 21, 1999

[54] APPARATUS AND METHOD FOR THE MEASUREMENT AND SEPARATION OF AIRBORNE FIBERS

[75] Inventor: Brian M. Ence, Lansdale, Pa.

[73] Assignee: CertainTeed Corporation, Valley Forge, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/743,554

[22] Filed: Nov. 4, 1996

[51] Int. Cl.⁶ .................................................. G01N 21/00
[52] U.S. Cl. ........................... 356/338; 356/340; 356/343
[58] Field of Search .................... 356/335, 343; 250/564, 573–574

[56] References Cited

U.S. PATENT DOCUMENTS

| | | | |
|---|---|---|---|
| 3,692,412 | 9/1972 | Chubb | 356/338 |
| 3,740,148 | 6/1973 | Moroz et al. | 356/336 |
| 4,249,244 | 2/1981 | Shofner et al. | . |
| 4,286,874 | 9/1981 | Smith et al. | 356/338 |
| 4,286,875 | 9/1981 | Smith | 356/338 |
| 4,473,296 | 9/1984 | Shofner et al. | 356/338 |
| 4,595,291 | 6/1986 | Tatsuno | . |
| 4,737,648 | 4/1988 | Smith et al. | 356/343 |
| 4,839,529 | 6/1989 | Fruengel | 250/574 |
| 4,916,325 | 4/1990 | Rood et al. | 250/573 |
| 4,940,327 | 7/1990 | Lilienfeld | 356/338 |
| 5,001,463 | 3/1991 | Hamburger | 340/627 |
| 5,270,787 | 12/1993 | Shofner et al. | 356/238 |
| 5,303,029 | 4/1994 | Sioma et al. | 356/339 |
| 5,319,575 | 6/1994 | Lilienfeld | 364/555 |
| 5,430,301 | 7/1995 | Shofner et al. | 250/461.1 |

OTHER PUBLICATIONS

*FM-7400 Real-Time Laser Fiber Monitor*, Monitoring Instruments for the Environment, Inc., Mar. 1991.

*Primary Examiner*—Robert H. Kim
*Attorney, Agent, or Firm*—Duane Morris & Heckscher LLP

[57] ABSTRACT

Apparatus and method for measuring the concentration of airborne fibers are provided. The apparatus includes a flow channel for providing laminar flow to a portion of the fibers in an air sample and a light source for generating a light beam directed to the laminarly flowing fibers to produce a scattered light. The apparatus further includes a sensor for sensing a portion of this scattered light and for producing an output from which a fiber concentration estimate can be measured.

54 Claims, 3 Drawing Sheets

APPARATUS AND METHOD FOR THE MEASUREMENT AND SEPARATION OF AIRBORNE FIBERS

CROSS-REFERENCE TO RELATED APPLICATION

This application is related to co-pending non-provisional U.S. patent application Ser. No. 08/743555, entitled "Device For Measuring The Dimension Of A Airborne Fiber", filed Nov. 4, 1996, which is assigned to the same assignee hereof, and is incorporated herein by reference.

FIELD OF THE INVENTION

This invention relates to methods and devices for estimating the concentration of airborne fibers, and particularly to devices which can decipher between respirable fibers and non-fiberous respirable fibers.

BACKGROUND OF THE INVENTION

At present, two primary methods for monitoring airborne fiber concentration exist. In the first method, airborne fibers are collected on a filter. This filter is analyzed by microscopy or chemical methods to determine the type of fibers present and to estimate airborne fiber concentration. This method suffers from the drawbacks of delayed availability of information, tediousness, inconvenience, high cost per sample, and lack of precision. Also, identification of fibers typically is performed by visual inspection, adding uncertainty to measurements for particular species of airborne fibers.

In the second method, real-time airborne fibers concentration is determined using optical techniques, in which light, attenuated by fibers passing by a light source, is analyzed. However, most of these devices do not discriminate between different species of airborne fibers and, in particular, may not provide an accurate measurement of potentially respirable fibers, particularly small glass fibers.

Because of the significant health problems posed by airborne asbestos fibers, current real-time airborne fiber monitors typically are aimed at selectively determining asbestos fiber concentration in an air sample having asbestos and other fibers. Because asbestos fibers exhibit paramagnetic properties, some existing devices preferentially align and oscillate asbestos fibers using, for example, a time-varying electric field quadrupole, a hybrid electric/magnetic field, or both. The induced oscillations tend to create a characteristic scattering of an impinging light, thus identifying the oscillating fiber as asbestos. Electrostatic techniques also may be used. Examples of such devices and methods for measuring airborne particulate concentration are found in U.S. Pat. No. 3,692,412 to Chubb (1972), entitled "Apparatus for Analyzing Suspended Particles"; in U.S. Pat. No. 4,940,327, to Lillienfeld (1990), entitled "Method and Apparatus for Real-Time Asbestos Monitoring"; and in U.S. Pat. No. 5,319,575, also to Lillienfeld (1994), entitled "System and Method for Determining and Outputting Airborne Particle Concentration." Also see MIE Fiber Monitor Model FM-7400 User's Manual by MIE, Inc., Billerica, Mass.

However, because potentially harmful respirable fibers including, for example, glass fibers, often do not exhibit paramagnetism, such methods may not be appropriate. What is needed, then, is an airborne fiber concentration measuring device that can accurately determine the concentration of respirable fibers suspended in an air sample, in real time, without the need for electrostatic, magnetic or hybrid electromagnetic components.

Additionally, the Lillienfeld's device is more complicated, detects only a small percentage of fibers in a given sample, and if the concentration of fibers in the sample is low or not representative of the fiber concentration in the air flow, measurement errors can result. There therefore remains a need for a fiber concentration measuring device which takes a more significant sampling of the fiber population and which is accurate at low concentration readings.

SUMMARY OF THE INVENTION

This invention provides devices and methods for measuring the concentration of airborne fibers in a fiber-containing air sample. The preferred device includes flow means for providing laminar flow to at least a portion of the fibers in the air sample. These laminarly flowing fibers are then illuminated with a light source to produce scattered light. A portion of the scattered light is then sensed to produce an output from which a fiber concentration estimate can be measured. Additionally, separation devices can be used to preselect fibers having a particular size, so as to measure only respirable fibers, for example. This invention provides an inexpensive way of measuring potentially hazardous respirable fibers in a work environment, such as a glass insulation or mat-making facility.

In a more detailed embodiment of this invention, a device is provided for analyzing air having respirable fibers, and non-respirable fibers or non-fibrous particulate matter, or both. This device includes separation means for selectively removing respirable fibers from non-respirable fibers to produce a filtered air sample containing aligned respirable fibers. These aligned fibers are then illuminated to produce scattered light, which is collected by a light sensor to produce an electrical output. The device further includes processing means for providing a concentration estimate for the respirable fibers from the output of the light sensor.

BRIEF DESCRIPTION OF THE DRAWINGS

The accompanying drawings, referenced to herein and constituting a part hereof, illustrate preferred embodiments of the device of the present invention and, together with the description, serve to explain the principles of the invention.

DETAILED DESCRIPTION OF THE INVENTION

Figure 1:
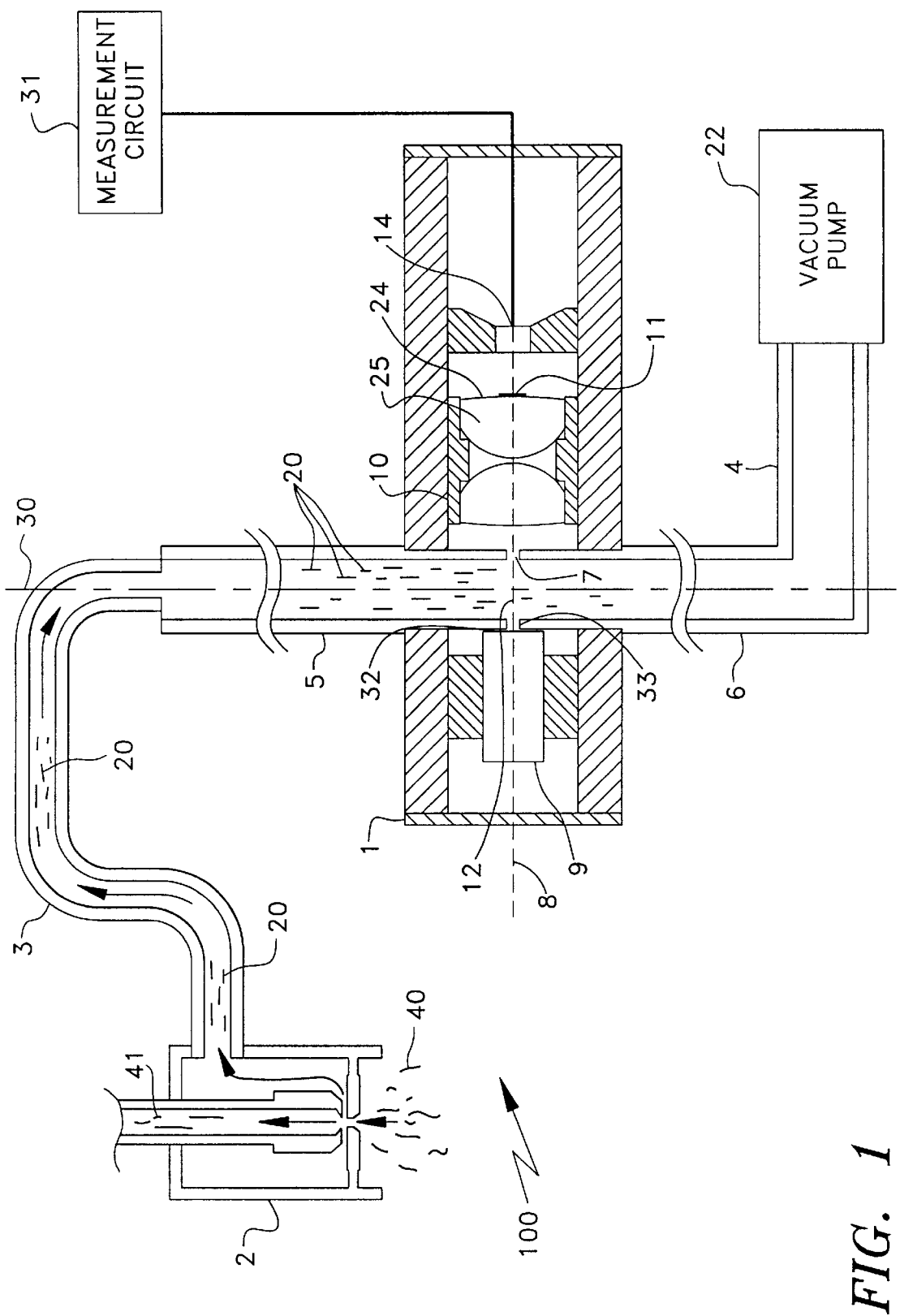
FIG. 1 is an illustration of an airborne fiber concentration measuring device in accordance with the present invention.

FIG. 1 illustrates one embodiment of the airborne fiber concentration measuring device 100 according to the principles of the invention herein. Device 100 can include a sensor 1 for detecting fibers and separation means, for example, virtual impactor 2, for separating respirable from non-respirable fibers or non-fibrous particulate matter. As used herein, "respirable fibers" means fibers which are less than about 3 $\mu$M in diameter, and preferably those with an aspect ratio of at least about 5:1 (length:diameter). Additionally, the term "light" refers to both visible and invisible electromatic waves, including x-ray and infrared.

A skilled artisan would recognize that virtual impactor 2 can use well-known techniques to separate the respirable particles from non-respirable particles, and therefore, the skilled artisan could employ other separating means for isolating respirable fibers from non-respirable fibers. One exemplary virtual impactor 2 that has been found suitable is shown in FIG. 1. This device takes in fiber-containing ambient air and draws off smaller respirable fibers 20 laterally at a venturi's mouth. Larger fibers 41, greater than about 3 μm, are drawn into the center tube of the virtual impactor 2.

In general, the air entering the device can have respirable fibers, non-respirable fibers, and other particulate matter mixed therein. Sensor 1 preferably senses aligned respirable fibers in the air but is substantially insensitive to the other non-fibrous particulate matter. In operation, respirable fibers 20 that may be present in the air are drawn from virtual impactor 2 through hose 3 which connects virtual impactor 2 to sensor 1. Air is drawn through the system by a small vacuum pump 22 to outlet 4 of lower flow tube 6. The air flow rate, and lengths and diameter of the upper and lower flow tubes 5, 6, are preferred to be such as to produce a laminar flow of air through tubes 5, 6. This laminar airflow tends to cause the fibers 20 in the air within tubes 5, 6 to become substantially aligned with the airflow and, hence, with the longitudinal axis 30 of flow tubes 5, 6. Flow tubes 5, 6 preferably are separated by a small gap 7 within sensor 1. Alternatively, a single tube having a pair of slots through its side wall perpendicular to its axis could work as well. This gap 7 is preferably positioned symmetrically about axis 8 of sensor 1. Flow tubes 5, 6 and gap 7 constitute the "flow channel" for this embodiment of the invention.

Within sensor 1 is a light source 9 which can be a coherent light source such as, for example, a diode laser. Light source 9 can produce a beam 12, preferably with a preselected cross-section along the beam path. It is preferred that light source 9 produce a collimated beam of light, ideally with an elliptical cross-section directed at light sensor 14. Light sensor 14 is preferred to be a photodetector. Beam 12 can be aimed along axis 8 of sensor 1 with the major axis of the ellipse of light preferably being substantially parallel to gap 8 between flow tubes 5, 6. The width of beam 12 need not be as wide as the diameter of flow tubes 5, 6.

A suitable light source for this embodiment can be, for example, a model LPM 03(670-5) laser diode from Power Technology, Inc., Little Rock, Ark. Similarly, a suitable photodetector is, for example, Devar Model 509-1, Bridgeport, Conn. A skilled artisan could employ other suitable light sources and light sensors to provide and detect light signals indicative of the presence of respirable fiber.

Figure 2:
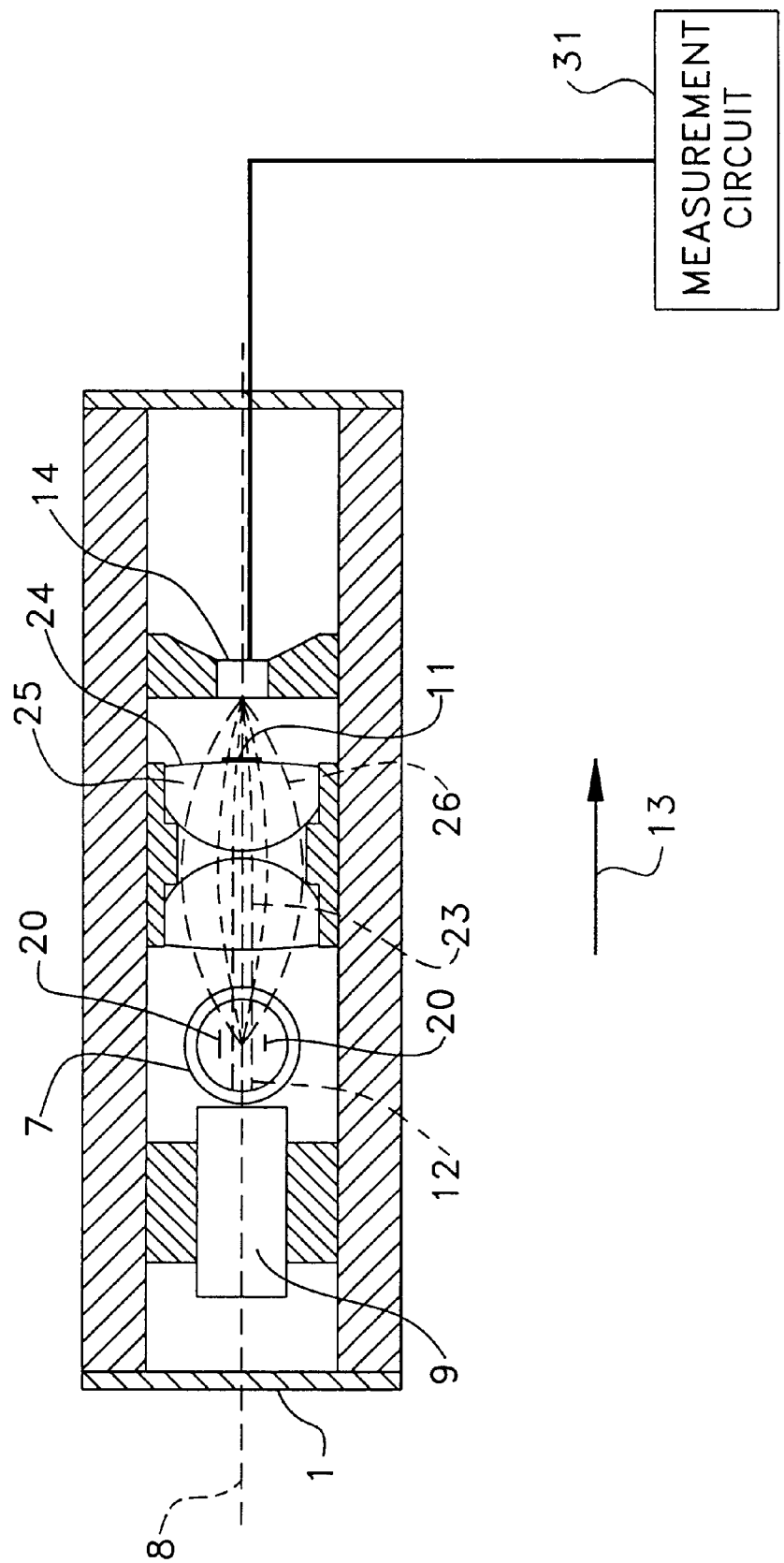
FIG. 2 is an illustration of one presently preferred embodiment of a sensor in accordance with the present invention.

FIG. 2 presents a cross-sectional view of a preferred sensor 1, which is positioned generally perpendicular to the airflow. After passing through gap 7, beam 12 enters an optical lens assembly 10. Lens assembly 10 can be a pair of condensing lenses, for example. This combination of lenses tends to have a short focal length, permitting a portion 23 of beam 12 to be directed to the back surface 24 of the second lens 25. Beam block 11 can be used to substantially block the collimated light 23 from being sensed by photodetector 14. It is preferred that the beam block 11 be umbrageously situated relative to photodetector 14 so that beam block 11 can shield photodetector 14 from light not indicative of the presence of a sensed fiber.

As fibers 20 pass though the beam 12 between the flow tubes 5, 6, some of the fibers 20 will scatter the light, as shown in FIG. 2. When a cylinder, such as a glass fiber, is illuminated at a normal incidence by light, it typically scatters the light in a preselected orientation in the flow channel, i.e. in a plane that is normal to the cylinder. Because fibers 20 have been aligned by the laminar airflow, these fibers 20 are generally oriented perpendicularly to the direction of beam 12. Therefore, beam 12 can be scattered in a plane that is generally parallel to planes formed by the ends of flow tubes 5, 6, thus permitting scattered light 26 to pass through gap 7 between flow tubes 5, 6.

Light that is scattered in a forward direction 13 can be collected by lens assembly 10 and focused on photodetector 14. Because this light typically is not collimated when it enters the lens assembly 10, it can be focused to a point some distance beyond lens assembly 10, thereby passing around beam block 11. Thus, while both the beam 12 and scattered light 26 enter lens assembly 10, beam 12 typically is blocked from impinging on photodetector 14 while scattered light 26 is, for the most part, focused onto the photodetector 14. Overall, only a small fraction of scattered light 26 is blocked by beam block 11.

It is preferred that photodetector 14 have a sensing region with a finite width which is wide enough to receive the scattered light 26. Within this width, it will respond to light scattered by fibers 20 that are some distance to either side of, as well as in front and in back of, axis 30 of flow tubes 5, 6. Therefore, fibers 20 are not required to pass through beam 12 single-file or closely aligned with axis 30. When beam 12 is scattered by fiber 20, it is focussed though lens assembly 10 to impinge upon photodetector 14, thus generating a brief electrical pulse therefrom. In general, the amplitude of this pulse is preferred to be proportional to the amount of light scattered by the fiber. The resultant pulse can be sent to an appropriate electronic measurement circuit 31 where the pulse is recorded. Using other quantitative information, such as, the flow rate of the air through sensor 1, and determining the rate at which the pulses are received, the concentration of respirable fibers in the air can be determined.

It is preferred that sensor 1 be substantially insensitive to non-fibrous particulate matter. Presently preferred embodiment of the current invention accomplish this selectivity by analyzing, for example, the optical differences between the typically cylindrical respirable fibers, and particulate matter having other shapes. That is, if a spherical or irregularly-shaped dust particle is drawn into sensor 1, the particulate matter will also scatter light from beam 12. However, such a particle tends to scatter light into a spherical volume. Much of this scattered light will impinge on, and be absorbed by the walls of flow tubes 5, 6.

In general, only a small fraction of the light scattered by these particles tends to pass through the gap 7 between flow tubes 5, 6. This small amount of scattered light tends to produce only a weak signal in photodetector 14. Circuit 31, receiving pulses from the photodetector 14, can be designed to ignore low amplitude pulses resulting from particulate matter. Therefore, device 100 can be made to respond only to respirable fibers while ignoring other non-fibrous particulate matter that may be present. Unlike prior art devices, the invention herein does not require the use of electrostatic or electromagnetic components to induce movement in the matter suspended in the air in order to determine whether or not the matter is a respirable fiber.

Indeed, the ability of device 100 to discriminate between respirable fibers and other particles relies on the following principles. First, non-respirable fibers are eliminated from the airflow by separation means, i.e. virtual impactor 2, before the air enters sensor 1. Second, the remaining fibers tend to be aligned with flow tube axis 30 by the laminar flow of air through tubes 5, 6. Third, beam 12 generally is oriented to be normal to the axis of tubes 5, 6. Fourth, light scattered by fibers 20 tends to be scattered in a plane which passes between the ends of flow tubes 5, 6, and a portion of the scattered light is focused onto photodetector 14. Fifth, light scattered by other particles tends to be scattered more omni-directionally than is the case with cylinders. Most of this light is absorbed by the walls of flow tubes 5, 6 and only a small amount of light remains to be focused on photodetector 14. Sixth, by discriminating between the amplitude of signals received from photodetector 14, device 100 can discriminate between fibers and other particles.

In FIGS. 1 and 2, lens assembly 10 and photodetector 14 are shown as being substantially in-line with, or in opposition to, beam 12. In view of the teachings of this invention, a skilled artisan would recognize that lens assembly 10 and photodetector 14 may be placed anywhere around axis 30 of flow tubes 5, 6, as long as they are still in the plane of light scattered from fibers 20. Although the amount of light collected by lens assembly 10 can depend upon the location of lens assembly 10, sensor 1 can discriminate between respirable fibers and other particles even with these alternative configurations.

Figure 3:
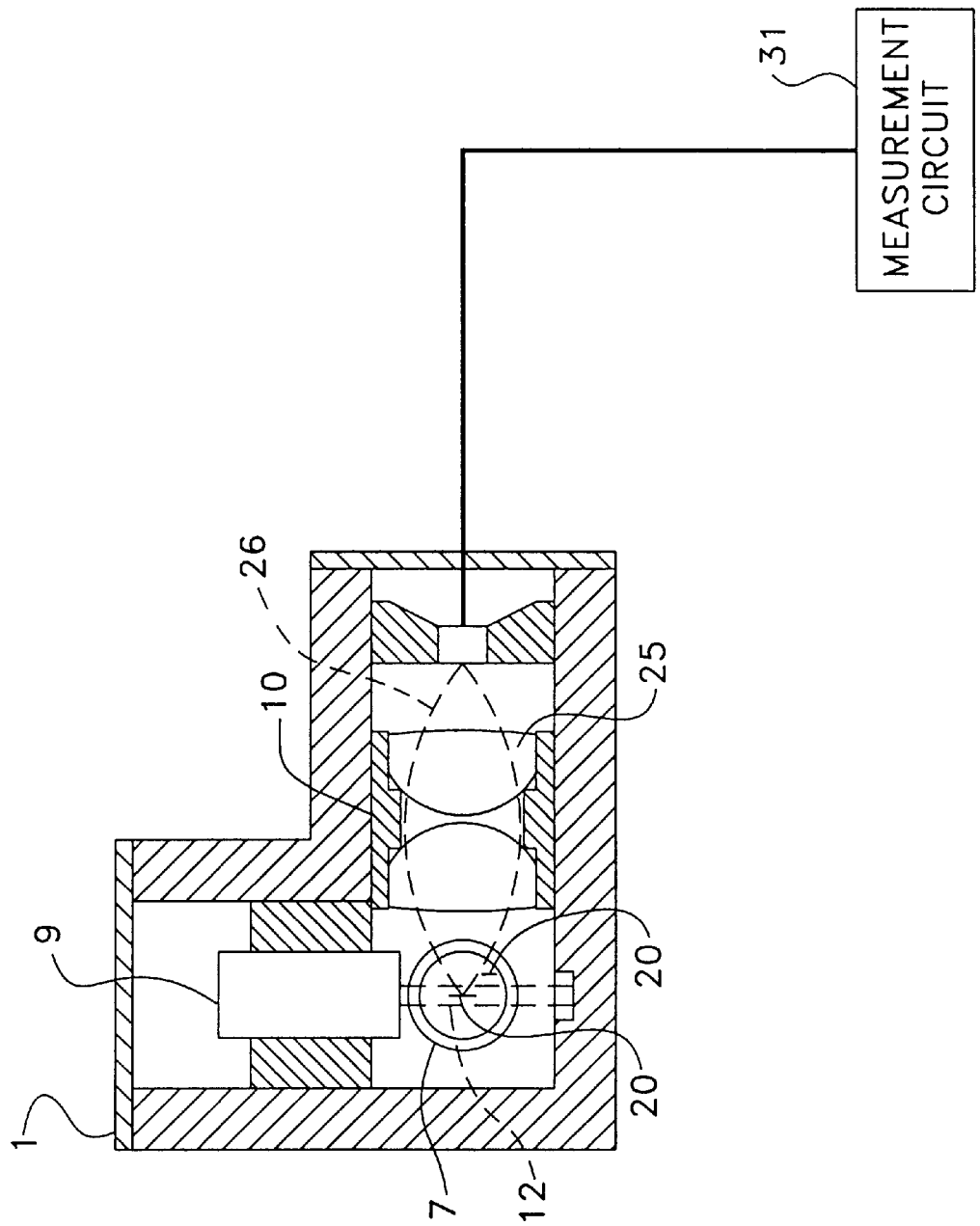
FIG. 3 is an illustration of another presently preferred embodiment of a sensor in accordance with the present invention.

In FIG. 3, for example, the components of device 100 are substantially the same as those in FIGS. 1 and 2, with the exception that lens assembly 10 and photodetector 14 have been rotated in orientation by 90 degrees. Also in FIG. 3, beam block 11 seen in FIGS. 1 and 2, may be eliminated because beam path 12 no longer is in-line with, or in opposition to, photodetector 14.

All publications mentioned in this specification are indicative of the level of skill of the skilled in the art to which this invention pertains. All publications are herein incorporated by reference to the same extent as if each individual publication was specifically but individually indicated to be incorporated by reference.

While specific embodiments of practicing the invention have been described in detail, it will be appreciated by those skilled in that art that various modifications and alternatives to those details could be developed in light of the overall teachings of the disclosure. Indeed, a skilled artisan would recognize that, although the invention has been described in terms of determining the concentration of airborne respirable fibers, the apparatus and method illustrated in detail herein also can be used to detect, characterize, and visualize other types of particles having specific optical properties. Accordingly, the particular arrangements of the methods and apparatus disclosed are meant to be illustrative only and not limiting to the scope of the invention, which is to be given the full breadth of the following claims, and any and all embodiments thereof.

What is claimed is:

1. A device for measuring the concentration of respirable airborne fibers in a fiber-containing air sample, said device comprising:
    a. flow means for providing linar flow to at least a portion of the fibers in said air sample, said laminarly flowing fibers being substantially aligned with an airflow;
    b. a light source for generating a light beam directed to said substantially aligned fiber portion to produce scattered light; and
    c. a light sensor for sensing a portion of said scattered light and for generating an output from which a fiber concentration estimate in said air sample can be measured.

2. The device of claim 1, wherein the sampled air includes non-fibrous particulate matter therein and the light sensor is substantially insensitive to the non-fibrous particulate matter.

3. The device of claim 1, wherein said device comprises a slotted opening for channeling scattered light to said light sensor.

4. The device of claim 1, wherein said light source comprises collimation means for providing a light beam having a preselected cross-section along a beam path.

5. The device of claim 4, wherein said flow means comprises a flow channel for receiving a plurality of laminarly flowing fibers, said flow channel having a longitudinal axis which is substantially normal to the beam path.

6. The device of claim 3, wherein said slotted opening is disposed to screen out scattered light which does not have a preselected orientation to the light sensor.

7. The device of claim 6, further comprising an optical lens for receiving a portion of the scattered light having a preselected orientation and for directing at least a portion of this scattered light to the light sensor.

8. The device of claim 7, further comprising a beam block located in a path of said light beam, said beam block being umbrageously situated relative to the light sensor, the beam block substantially blocking the light beam from the light sensor.

9. An fiber concentration measuring device for analyzing air having respirable fibers, non-respirable fibers and/or non-fibrous particulate matter, the device comprising:
    a. separation means for selectively removing the respirable fibers from said non-respirable fibers to produce a filtered air sample containing respirable fibers;
    b. flow means coupled to the separation means providing a substantially laminar flow to said respirable fibers, said laminarly flowing respirable fibers being substantially aligned with an airflow;
    c. a light source for illuminating a portion of said substantially aligned laminarly flowing respirable fibers with a light beam to produce scattered light;
    d. a light sensor for selectively sensing a portion of said scattered light to produce an electrical output; and
    e. processing means for providing an estimate of a concentration of said respirable fibers which is derived from said output.

10. The device of claim 9, wherein said light sensor comprises a photodetector for detecting said portion of said scattered light only in a preselected orientation.

11. The device of claim 10, further comprising a collimation means for providing a preselected cross-section to said light beam.

12. The device of claim 11, further comprising a flow channel for receiving said laminarly flowing respirable fibers, the longitudinal axis of the flow channel being substantially normal to a beam path of said light beam, said laminarly flowing respirable fibers reflecting a scattered light having a preselected orientation.

13. The device of claim 12 wherein the light beam is a collimated laser light beam and the preselected cross-section is elliptical.

14. The device of claim 9 further comprising an optical lens for receiving said scattered light portion and for directing it to the light sensor.

15. The device of claim 14, further comprising a beam block located in the light beam path, the beam block being umbrageously situated relative to the light sensor, the beam block substantially blocking the collimated light from the light sensor.

16. The device of claim 15, wherein the light source is a laser, and said respirable fibers contain glass fibers.

17. The device of claim 16, wherein the flow means comprises first and second flow tubes having a gap there between, said gap being generally positioned between the light source and the light sensor for passage of the light beam therethrough.

18. A device for providing an estimate of a concentration of airborne fibers in a fiber-containing air sample having respirable fibers, non-respirable fibers and/or particulate matter, the device comprising:
   a. separation means for selectively removing a plurality of non-respirable fibers present in said air sample to produce a filtered air sample having a plurality of laminarly flowing respirable fibers therein; and
   b. optical sensor means for selectively sensing said plurality of laminarly flowing respirable fibers in the filtered air sample, said optical sensor means having a flow tube including a longitudinal axis, said laminarly flowing respirable fibers being aligned generally parallel with the longitudinal axis of said flow tube, said optical sensor means having an inlet connected to said separation means and an outlet, said optical sensor means including:
      a collimated light source for projecting a light beam having a pre-selected cross-section along a beam path into said laminarly flowing respirable fibers to produce a scattered light;
      optical lens means for receiving and focusing a portion of said scattered light;
      photodetector means for receiving said focused portion of said scattered light and for producing an electrical output;
      processing means for receiving said electrical output from said photodetector mean and for producing an estimate of a concentration of said respirable fibers in said air sample.

19. The device of claim 18, wherein said photodetector means is oriented generally opposite to the collimated light source and is disposed at least partially in the beam path, said device further comprising a beam block located in the beam path, the beam block being umbrageously situated relative to the photodetector means for substantially blocking the light beam from impinging upon the photodetector.

20. A method of measuring the concentration of airborne fibers in a fiber-containing air sample, comprising:
   a. providing laminar flow to at least a portion of the fibers in said air sample, said laminarly flowing respirable fibers being substantially aligned with an airflow;
   b. directing a light beam at said substantially aligned laminarly flowing fibers to produce a scattered light; and
   c. sensing a portion of said scattered light and generating an output from which a fiber concentration estimate can be produced.

21. A device for measuring the concentration of airborne fibers in a fiber-containing air sample, said device comprising:
   a. flow means for providing laminar non-oscillating flow to at least a portion of the fibers in said air sample,
   b. a light source for generating a light beam directed to said non-oscillating fiber portion to produce scattered light; and
   c. a light sensor for sensing a portion of said scattered light and for generating an output from which a fiber concentration estimate in said air sample can be measured.

22. The device of claim 21, wherein the sampled air includes non-fibrous particulate matter therein and the light sensor is substantially insensitive to the non-fibrous particulate matter.

23. The device of claim 21, wherein said device comprises a slotted opening for channeling scattered light to said light sensor.

24. The device of claim 21, wherein said light source comprises collimation means for providing a light beam having a preselected cross-section along a beam path.

25. The device of claim 24, wherein said flow means comprises a flow channel for receiving a plurality of laminarly flowing fibers, said flow channel having a longitudinal axis which is substantially normal to the beam path.

26. The device of claim 23, wherein said slotted opening is disposed to screen out scattered light which does not have a preselected orientation to the light sensor.

27. The device of claim 26, further comprising an optical lens for receiving a portion of the scattered light having a preselected orientation and for directing at least a portion of this scattered light to the light sensor.

28. The device of claim 27, further comprising a beam block located in a path of said light beam, said beam block being umbrageously situated relative to the light sensor, the beam block substantially blocking the light beam from the light sensor.

29. An fiber concentration measuring device for analyzing air having respirable fibers, non-respirable fibers and/or non-fibrous particulate matter, the device comprising:
   a. separation means for selectively removing the respirable fibers from said non-respirable fibers to produce a filtered air sample containing respirable fibers;
   b. flow means coupled to the separation means providing a substantially laminar non-oscillating flow to said respirable fibers;
   c. a light source for illuminating a portion of said non-oscillating laminarly flowing respirable fibers with a light beam to produce scattered light;
   d. a light sensor for selectively sensing a portion of said scattered light to produce an electrical output; and
   e. processing means for providing an estimate of a concentration of said respirable fibers which is derived from said output.

30. The device of claim 29, wherein said light sensor comprises a photo detector for detecting said portion of said scattered light only in a preselected orientation.

31. The device of claim 30, further comprising a collimation means for providing a preselected cross-section to said light beam.

32. The device of claim 31, further comprising a flow channel for receiving said laminarly flowing respirable fibers, the longitudinal axis of the flow channel being substantially normal to a beam path of said light beam, said laminarly flowing respirable fibers reflecting a scattered light having a preselected orientation.

33. The device of claim 32 wherein the light beam is a collimated laser light beam and the preselected cross-section is elliptical.

34. The device of claim 29 further comprising an optical lens for receiving said scattered light portion and for directing it to the light sensor.

35. The device of claim 34, further comprising a beam block located in the light beam path, the beam block being umbrageously situated relative to the light sensor, the beam block substantially blocking the collimated light from the light sensor.

36. The device of claim 35, wherein the light source is a laser, and said respirable fibers contain glass fibers.

37. The device of claim 36, wherein the flow means comprises first and second flow tubes having a gap there between, said gap being generally positioned between the light source and the light sensor for passage of the light beam therethrough.

38. A device for measuring the concentration of airborne fibers in a fiber-containing air sample, said device comprising:
 a. flow means for providing laminar flow to at least a portion of the fibers in said air sample, said flow means comprising a flow channel for receiving a plurality of laminarly flowing fibers, said flow channel having a longitudinal axis;
 b. a light source for generating a light beam directed to said fiber portion to produce scattered light, said light beam having a beam path, said longitudinal axis of said flow channel being substantially normal to said beam path; and
 c. a light sensor for sensing a portion of said scattered light and for generating an output from which a fiber concentration estimate in said air sample can be measured.

39. The device of claim 38, wherein the sampled air includes non-fibrous particulate matter therein and the light sensor is substantially insensitive to the non-fibrous particulate matter.

40. The device of claim 38, wherein said device comprises a slotted opening for channeling scattered light to said light sensor.

41. The device of claim 38, wherein said light source comprises collimation means for providing a light beam having a preselected cross-section along a beam path.

42. The device of claim 40, wherein said slotted opening is disposed to screen out scattered light which does not have a preselected orientation to the light sensor.

43. The device of claim 42, further comprising an optical lens for receiving a portion of the scattered light having a preselected orientation and for directing at least a portion of this scattered light to the light sensor.

44. The device of claim 43, further comprising a beam block located in a path of said light beam, said beam block being umbrageously situated relative to the light sensor, the beam block substantially blocking the light beam from the light sensor.

45. A fiber concentration measuring device for analyzing air having respirable fibers, non-respirable fibers and/or non-fibrous particulate matter, the device comprising:
 a. separation means for selectively removing the respirable fibers from said non-respirable fibers to produce a filtered air sample containing respirable fibers;
 b. flow means coupled to the separation means providing a substantially laminar flow to said respirable fibers;
 c. a light source for illuminating a portion of said laminarly flowing respirable fibers with a light beam to produce scattered light;
 d. a flow channel for receiving said laminarly flowing respirable fibers, the longitudinal axis of the flow channel being substantially normal to a beam path of said light beam;
 e. a light sensor for selectively sensing a portion of said scattered light to produce an electrical output; and
 f. processing means for providing an estimate of a concentration of said respirable fibers which is derived from said output.

46. The device of claim 45, wherein said light sensor comprises a photo detector for detecting said portion of said scattered light only in a preselected orientation.

47. The device of claim 46, further comprising a collimation means for providing a preselected cross-section to said light beam.

48. The device of claim 47, wherein the light beam is a collimated laser light beam and the preselected cross-section is elliptical.

49. The device of claim 45, further comprising an optical lens for receiving said scattered light portion and for directing it to the light sensor.

50. The device of claim 49, further comprising a beam block located in the light beam path, the beam block being umbrageously situated relative to the light sensor, the beam block substantially blocking the collimated light from the light sensor.

51. The device of claim 50, wherein the light source is a laser, and said respirable fibers contain glass fibers.

52. The device of claim 45, wherein the flow means comprises first and second flow tubes having a gap there between, said gap being generally positioned between tle light source and the light sensor for passage of the light beam therethrough.

53. A method of measuring the concentration of airborne fibers in a fiber-containing air sample, comprising:
 a. providing non-oscillating laminar flow to at least a portion of the fibers in said air sample;
 b. directing a light beam at said non-oscillating laminarly flowing fibers to produce a scattered light; and
 c. sensing a portion of said scattered light and generating an output from which a fiber concentration estimate can be produced.

54. A method of measuring the concentration of airborne fibers in a fiber-containing air sample containing respirable fibers and other matter, comprising the steps of:
 a. providing laminar flow to at least a portion of the fibers in said air sample, said portion containing respirable fibers and other matter;
 b. directing a light beam at said laminarly flowing fibers and other matter to produce a scattered light;
 c. sensing a portion of said scattered light;
 d. providing first and second pulse signals corresponding to the detection of light from a respirable fiber and other matter respectively, said first and second pulse signals having first and second amplitudes;
 e. discriminating between said first and second amplitudes to provide a signal representative of a concentration of respirable fibers in said air sample.

* * * * *